United States Patent [19]

Chen et al.

[11] Patent Number: 5,466,787
[45] Date of Patent: Nov. 14, 1995

[54] PROCESS FOR PREPARING AZT

[75] Inventors: Bang-Chi Chen, East Syracuse; Sandra L. Quinlan, Manlius, both of N.Y.

[73] Assignee: Bristol-Myers Squibb Company, Del.

[21] Appl. No.: 152,803

[22] Filed: Nov. 15, 1993

[51] Int. Cl.$^6$ .............................. C07H 1/00; C07H 19/173
[52] U.S. Cl. .................. 536/55.3; 536/28.4; 536/28.54
[58] Field of Search ................................ 536/55.3, 28.53, 536/28.54, 28.55

[56] References Cited

U.S. PATENT DOCUMENTS

| | | | |
|---|---|---|---|
| 3,202,656 | 8/1965 | Abraham et al. | 540/230 |
| 4,724,232 | 2/1988 | Rideout et al. | 514/50 |
| 4,780,453 | 10/1988 | Rideout et al. | 514/50 |
| 4,810,796 | 3/1989 | Luksza | 546/335 |
| 4,818,538 | 4/1989 | Rideout et al. | 424/436 |
| 4,818,750 | 4/1989 | Rideout et al. | 514/50 |
| 4,828,838 | 5/1989 | Rideout et al. | 424/451 |
| 4,847,244 | 7/1989 | Rideout et al. | 514/50 |
| 4,874,609 | 10/1989 | Rideout et al. | 424/85.4 |
| 4,874,751 | 10/1989 | Beacham, III et al. | 514/50 |
| 4,916,218 | 4/1990 | Almond et al. | 536/18.2 |
| 4,921,950 | 5/1990 | Wilson | 536/28.54 |
| 5,041,543 | 8/1991 | Shaver et al. | 536/28.2 |
| 5,093,114 | 3/1992 | Rideout et al. | 424/85.4 |
| 5,145,840 | 9/1992 | Kirk, III et al. | 514/49 |
| 5,175,306 | 12/1992 | Geiger et al. | 548/452 |

FOREIGN PATENT DOCUMENTS

| | | |
|---|---|---|
| 0280128A2 | 8/1988 | European Pat. Off. . |
| 0292101 | 11/1988 | European Pat. Off. . |
| 0295090 | 12/1988 | European Pat. Off. . |
| 0325537A1 | 7/1989 | European Pat. Off. . |
| 1460131 | 2/1967 | France . |
| 2290444 | 6/1976 | France . |
| 1080904 | 8/1967 | United Kingdom . |
| 90/01492 | 2/1990 | WIPO . |
| WO93/07162 | 4/1993 | WIPO . |

OTHER PUBLICATIONS

Hrebabecky et al. Carbohydrate Res. 216:179–186, 1991.

Horwitz, et al., "Nucleosides. V. The Monomesylates of 1-(2'-Deoxy-β-D-lyxofuranosyl)thymine," *J. Org. Chem.*, 29, 1964, 2076–2079.

Maillard, et al., "Synthesis of 3'-Substituted-2',3'-dideoxynucleoside Analogs as Potential Anti-AIDS Drugs," *Tetrahedron Letters*, 30, 1989, 1955–1958.

Chu, et al., "An Efficient Total Synthesis of 3'-Azido-3'-deoxythimidine (AZT) and 3'-Azido-Azido-2',3'-dideoxyuridine (AZDDU, CS-87) From D-Mannitol," *Tetrahedron Letters*, 29, 1988, 5349–5352.

Fleet, et al., "Methyl 5-O-tert-butyldiphenylsilyl-2-deoxy-αβ-D-threo- pentofuranoside as a Divergent Intermediate for the Synthesis of 3'-Substituted-2',3'-dideosynucleosides: Synthesis of 3'-Azido-3'-deoxythimidine, 3'-Deoxy-3'-fluoro-thymidine and 3'-Cyano-3'-Cyano-3'-deoxythimidine," *Tetrahedron*, 44, 1988, 625–636.

Wengel, et al., "Selective Deformylation of an α,β-Unsaturated Sugar aldehyde in a Very Short Synthesis of 3'-Azido-3'-3'-deoxythymidine (AZT) and is Stereoisomers," *Synthesis*, Jun. 1991, 451.

Hager, et al., "Cyclization Protocols for Controlling the Glycosidic Stereochemistry of Nucleosides. Application to the Synthesis of the antiviral Agent 3'-Azido-3'-Azido-3'-Deoxythymidine (AZT)," *J. Am. Chem. Soc.*, 113, 1991, 5117–5119.

Jung, et al, "Synthetic Approaches to 3'-Azido-3'-3'-deoxythymidine and Other Modified Nucleosides," *J. Org. Chem.*, 56, 1991, 2614–2615.

Sugimura, et al., "Coupling Reaction of 1-thiopentofuranosides With Silylated Pyrimidine Bases by Activation with N-Bromosuccinimide:Synthesis of 3',-Azido-3'-deoxythymidine and Its Related Nucleoside Analogs," *Tetrahedron Letters*, 32, 1991, 1813–1816.

Czernecki, et al., "An Efficient Synthesis of 3'-Azido-3'-deoxythymidine (AZT)," *Synthesis*, Mar. 1991, 239–240.

Chemical Abstracts, Abstract No. 158908 vol. 105, No. 17, p. 380, column R Oct. 27, 1986 (JP-A 61 70 999).

*Primary Examiner*—Douglas W. Robinson
*Assistant Examiner*—Gary L. Kunz
*Attorney, Agent, or Firm*—Thomas R. Savitsky

[57] ABSTRACT

A process for preparing AZT and comprising the steps of:

a) reacting a 2'-halo-5'-protected pyrimidinyl 2'-deoxyribonucleoside having a 3'-sulfonyl group with tributyl tin hydride and catalytic amount of azobisisobutyronitrile in an ether, ester, or ketone solvent to yield a dehalogenated pyrimidinyl 2'-deoxyribonucleoside; followed by b) reacting said dehalogentated pyrimidinyl 2'-deoxynucleoside formed in step (a) with a base, a lithium salt, and an azide salt to yield a 5'-protected pyrimidinyl 3'-dideoxy-3' -azido-ribonucleoside; and c) deprotecting the nucleoside derivative of step (b) to yield 3'-dideoxy-3'-azidothymidine.

20 Claims, No Drawings

5,466,787

PROCESS FOR PREPARING AZT

FIELD OF THE INVENTION

The present invention concerns a process for preparing AZT and derivatives thereof.

BACKGROUND OF THE INVENTION

The compound AZT (3'-azido-3'-deoxythymidine) and derivatives thereof are known to be useful for treating viral and bacterial infections, most notably in the treatment of AIDS (see, for example, U.S. Pat. Nos. 4,724,232, 4,828,838, 4,847,244, 4,874,609, 4,874,751, 4,818,750, 5,093,114 and 5,145,840). In the past, AZT has been made from an expensive starting material, thymidine (see Horwitz, J. P., et al., *J. Org. Chem.*, 1964, 29, 2076; Maillard, M. Farag, A., Frappier, F., Florent, J. C., Grierson, D. S., Monneret, C., *Tetrahedron Lett.*, 1989, 30, 1955; U.S. Pat. No. 5,041,543 and DE 3,705,794).

Another known approach for preparing AZT features the coupling between an azido substituted carbohydrate precursor with an activated thymine base (see, Chu, C. K., Beach, J. W., Ullas, G. V., Kosugi, Y., *Tetrahedron Lett.*, 1988, 29, 5349; Chu, C. K., WO 9001492 A1, February 1990; Fleet, G. W. J., Son, J. C., Derome, A. E., *Tetrahedron*, 1988, 44, 625; Wengel, J., Pedersen, E. B., *Synthesis*, 1991, 451; Hager, M. W., Liotta, D. C., *J. Am. Chem. Soc.*, 1991, 113, 5117; Jung, M. E., Gardiner, J. M., *J. Org. Chem.*, 1991, 56, 2614; and Sugimura, H., Osumi, K., Yamazaki, T., Yamaya, T., *Tetrahedron Lett.*, 1991, 32, 1813).

A third approach employs D-xylose (see, U.S. Pat. No. 4,916,218, Japanese Patent 63255295, European Patent 295090, and U.S. Pat. No. 4,921,950) or D-glucofuranose (see, Hrebabecky, H., Holy, A., *Carbohydr. Res.*, 1991, 216, 179) as starting material, using the 2'-α-hydroxy group (in carboxylic ester form) to direct the base coupling to give the required β-anomer. Although the glycosidic stereoselectivity of this reaction is high, the lengthy selective protection and deprotection of the sugar moieties remained a problem, in addition to the expensive reagents used in these processes.

SUMMARY OF THE INVENTION

The inventors have discovered a new, economical and highly efficient process for producing AZT and derivatives thereof as well as key intermediates. The process involves novel intermediate compounds and can be adapted to produce other pharmaceutically useful nucleosides.

The present invention makes use of key intermediate steps. One such intermediate step can be described as a process for reduction of a pyrimidinyl 2'-deoxyribonucleoside compound comprising contacting a 2'-halo-5'-protected pyrimidinyl 2'-deoxyribonucleoside compound having a 3'α-sulfonyl group with a tri-$C_1$–$C_{12}$ alkyl tin hydride reducing agent and a catalytic amount of a radical initiator in an ether, ester or ketone solvent under conditions to result in a dehalogenated pyrimidinyl 2'-deoxyribonucleoside compound (referred to herein as the "reduction step").

The reduction step is optionally followed by another key intermediate step which can be described as a one-step process for displacing a 3'α-sulfonyl group of a pyrimidinyl 2'-deoxyribonucleoside compound comprising contacting a pyrimidinyl 2'-deoxyribonucleoside compound having a 3'α-sulfonyl group with a base, a lithium salt, and an azide salt under conditions to result in formation of a 5'-protected pyrimidinyl 2',3'-dideoxyribonucleoside compound having a 3'α-azido group (referred to herein as the "displacement step").

The displacement step is optionally followed by a step to remove the 5'-protecting group in order to produce AZT or an active derivative thereof.

DETAILED DESCRIPTION OF THE INVENTION

Use of the intermediates and processes of the invention yield AZT and other useful nucleosides via reactions having good yields and relatively few undesired by-products.

The use of 5-methyluridine instead of thymidine as a starting material is less costly.

Further advantages and various other aspects of the invention will be apparent after consideration of the following description and claims.

Unless otherwise indicated, all percentages recited are weight percentages, based upon total composition weight.

All previously published materials referred to herein are hereby incorporated by reference in their entirety.

A key intermediate for use herein is a 2'-halo-5'-protected pyrimidinyl 2'-deoxyribonucleoside compound. A preferred such compound is of the formula

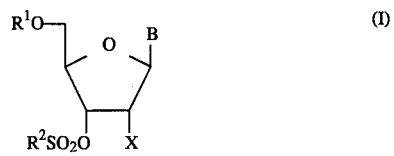

wherein $R^1$ is hydrogen or an OH-protecting group, $R^2$ is $C_1$–$C_{12}$ alkyl (preferably $C_1$–$C_6$ alkyl) or $C_6$–$C_{30}$ aryl, B is a pyrimidine base; and X is Cl, Br or I.

Unless otherwise indicated, as used herein the term "alkyl" or derivative forms thereof refers to straight chain or branched alkyl groups of 1 to 12 carbon atoms, the term "aryl" or derivative forms thereof refers to aryl groups of 6 to 30 carbon atoms, the term "acyl" refers to acyl groups of 1 to 12 carbon atoms, and the term "halo" refers to Cl, Br and I. Examples of alkyl groups include methyl, ethyl, propyl, butyl, isobutyl, pentyl, hexyl, and the like. Examples of aryl groups include phenyl, naphthyl, anthryl, biphenyl and the like. Examples of acyl groups include acetyl, benzoyl, and the like.

The pyrimidine base ("B group") is typically a nucleobase group containing a keto group in the 2-position, especially a thymine, uracil or cytosine group. Preferred B groups include

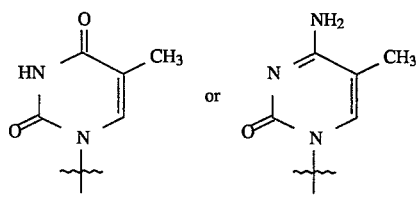

abbreviated herein as "Bz") is highly preferred.

The compound of formula II is preferred. Formula II is:

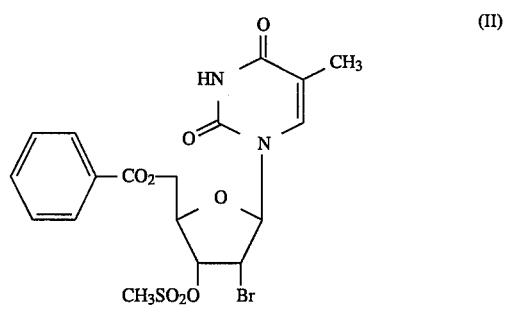

By "hydroxyl-protecting group" or "OH-protecting group" is meant a group which protects the hydroxyl group, is capable of being introduced and removed, and does not substantially interfere with the desired reactions. Preferred OH-protecting groups are carboxylic ester groups, carbonate groups, silyl groups, acetal and ketal groups and ether groups. Examples of such OH-protecting groups include RC(O)—, ROC(O)—, $R_3$Si—, ROCH$_2$ and R—, when R is alkyl or aryl. Preferred OH-protecting groups are ester (i.e., RC(O)—) groups. The benzoyl group (PhC(O); sometimes This compound is produced via the reactions set out schematically on the following page.

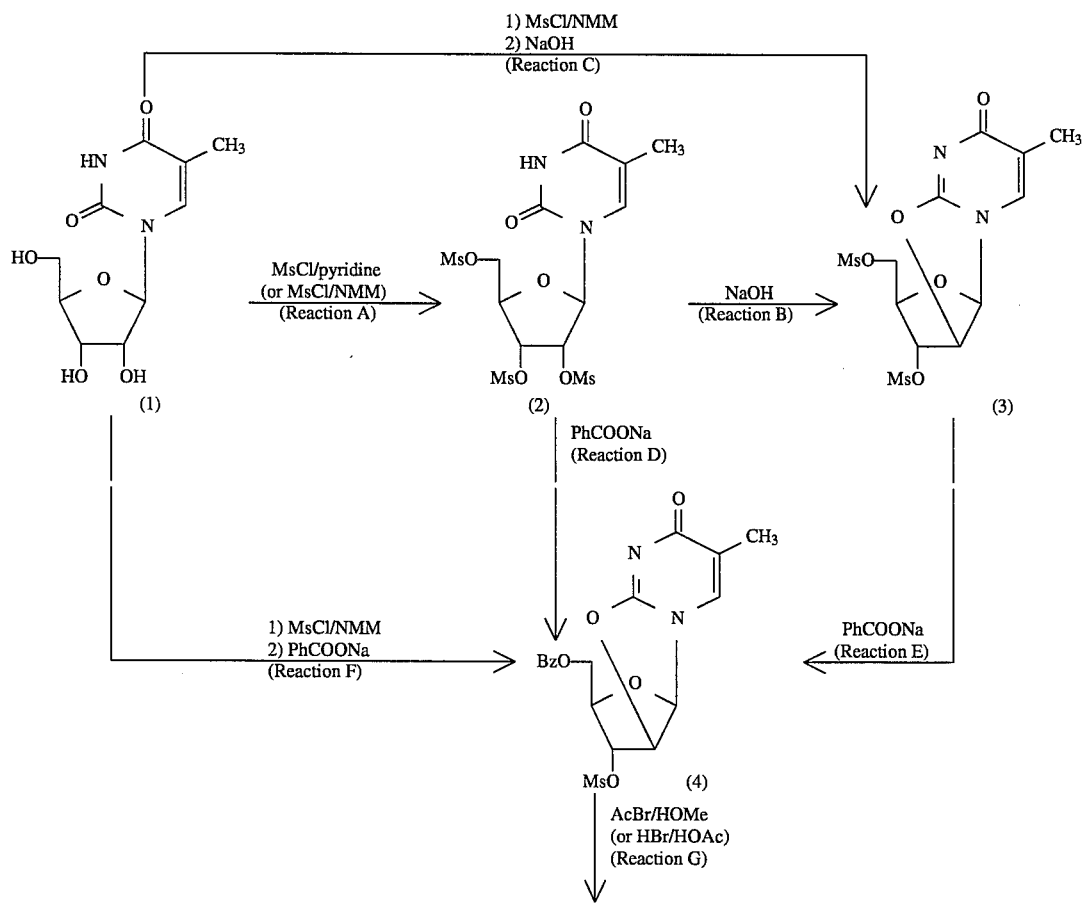

-continued
Scheme 1

Me = methyl
Bz = benzoyl
Ms = methanesulfonyl
NMM = N-methylmorpholine
Ph = phenyl
Ac = acetyl

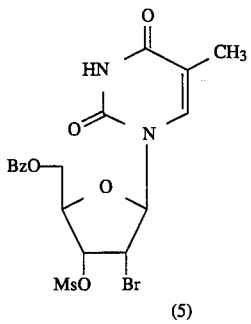

(5)

The compound of formula II (i.e., compound 5 in Scheme 1) can be made via several routes. Scheme 1 shows a variety of such routes. Among the routes illustrated are reaction sequences as follows:

1. Reactions A, D, and G;
2. Reactions F and G;
3. Reactions A, B, E and G;
4. Reactions C, E and G.

Other conventional reactions, as well as modifications of those discussed here, may be used to produce compound 5.

A preferred process for producing the 2'-halo-5'-protected pyrimidinyl 2'-deoxyribonucleoside intermediate can be described as a process comprising the steps of:

(a) contacting a 2'α,3'α,5'-trihydroxy pyrimidinyl ribonucleoside with a $C_1$–$C_{12}$ alkyl or $C_6$–$C_{30}$ aryl sulfonyl chloride and a base under conditions to form a tris-(alkylsulfonyl) or tris(arylsulfonyl) compound;

(b) contacting the compound formed in step (a) with a base under conditions to form a 2,2'-anhydro compound;

(c) contacting the compound formed in step (b) with a metal carboxylate to yield a 5'-carboxylic ester compound;

(d) contacting the compound formed in step (c) with a hydrohalic acid to produce a 2'-halo-3'-sulfonyl-5'-carboxylic diester compound.

The schematic representation of this series of reactions is:

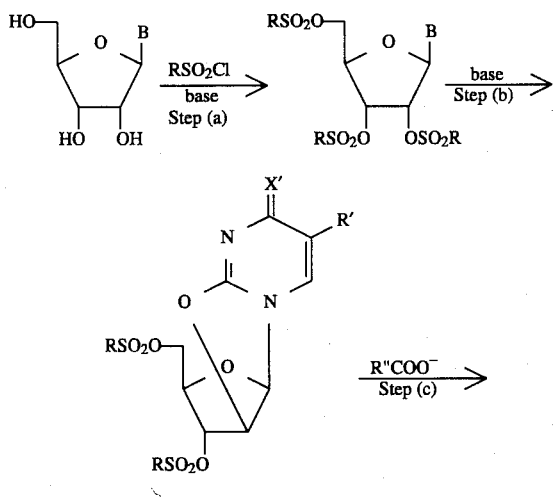

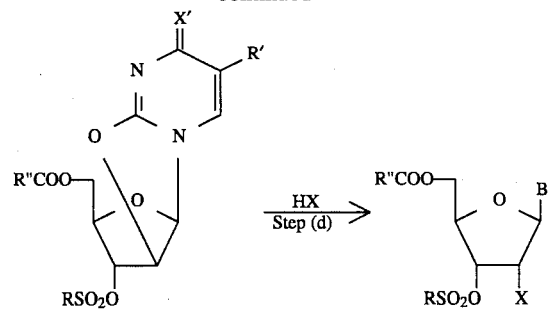

B = pyrimidine base
R = alkyl, or aryl
X' = O, NH, S
X = Cl, Br, I
R' = H, alkyl, aryl, or halo
R" = H, alkyl, or aryl In step (a), useful alkyl and arylsulfonyl halides include methanesulfonyl chloride, phenylsulfonyl chloride and the like. Methanesulfonyl chloride ($CH_3SO_2Cl$) is highly preferred.

The base used in step (a) is generally an organic amine. Preferred compounds include pyridine, N-methyl-morpholine and the like.

The basic reagent used in step (b) is typically a strong base. Preferred compounds are one or more inorganic bases such as sodium or potassium hydroxide and sodium and potassium carbonate. Sodium hydroxide, NaOH, is highly preferred.

Step (c) is generally carried out using as the metal carboxylate, alkali metal salts of carboxylic acids. Sodium and potassium benzoate are preferred agents.

The hydrohalic acid used in step (d) is generally selected from HCl, HBr and HI, with HBr preferred. The hydrohalic acid can be generated and used in situ.

The reduction step of the invention is performed using the 2'-halo-5'-protected pyrimidinyl 2'-deoxyribonucleoside intermediate as a starting material. The pyrimidinyl 2'-deoxyribonucleoside starting compound for the reduction step has a 3'α-sulfonyl group. Examples of 3'α-sulfonyl groups include $C_1$–$C_{12}$ alkylsulfonyl, $C_6$–$C_{30}$ arylsulfonyl, and the like. The pyrimidinyl 2'-deoxyribonucleoside starting compound of the reduction step is preferably a thymidine derivative. The reduction step requires the use of a radical initiator such as azobisisobutyronitrile (AIBN), diacetyl peroxide, t-butyl peracetate, di-t-butyl peroxide, benzoyl peroxide, or any other suitable compounds known in the art to initiate free radical formation. It is important to the invention that a the solvent used in the reduction step is an ether, ester, or ketone. It has been found that use of such a solvent avoids substantial formation of an anhydro impurity. An example of such an anhydro impurity has the following formula

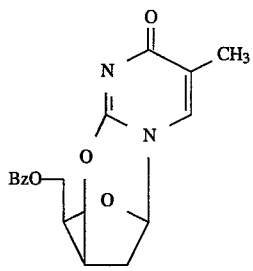

We have found that when the 3'-sulfonyl group is in the α-position, then use of certain solvents such as dimethylformamide (DMF) results in substantial formation of the anhydro impurity. The anhydro impurity problem does not arise in prior art processes such as described in U.S. Pat. No. 4,921,950 since the 3'-sulfonyl group is in the β-position. Solvents which consistently provide low levels of the anhydro impurity are within the scope of the present invention. Such solvents are ethers, esters, and ketones which use results in low levels of the anhydro impurity, for example, less than 0.5% anhydro impurity formation, preferably less than 0.05%.

Suitable ether solvents for the reduction step contain two to ten carbon atoms. Such ethers may contain more than one oxygen atom (e.g., two or three). Examples of such ethers include $C_1$–$C_6$ dialkyl ethers, preferably $C_1$–$C_4$ dialkyl ethers, such as dibutyl ether, diethyl ether, methyl t-butyl ether, and the like. Other examples of suitable ethers include $C_4$–$C_6$ cyclic ethers such as tetrahydrofuran (THF), dioxane, and the like.

Suitable ester solvents for the reduction step are alkyl esters and contain two to ten carbon atoms, preferably two to six carbon atoms. Examples include methyl acetate, ethyl acetate (sometimes abbreviated herein as "EtOAc"), butyl acetate, propyl acetate, isopropyl acetate, t-butyl acetate, isobutyl acetate, s-butyl acetate, ethyl formate, and the like.

Suitable ketone solvents for the reduction step are dialkyl ketones containing three to ten carbon atoms, preferably three to six carbon atoms. Examples include acetone, butanone, pentanone, methyl isobutyl ketone, and the like.

The reduction step also requires a tri $C_1$–$C_{12}$ alkyl tin hydride reducing agent (preferably a $C_1$–$C_4$ alkyl tin hydride reducing agent). Most preferred is tri-butyl tin hydride ($Bu_3SnH$). Preferred 5'-protecting groups are carboxylic esters especially benzoyl. The most preferred 2'-halo group is bromine. The process conditions for the reduction step are not particularly critical and can vary considerably. For example, a temperature of about 40° C. to about 155° C. (preferably about 50° C. to about 125° C.) for about 0.25 to about 5 hours is typically adequate.

The amount of reducing agent should be sufficient to allow the reaction to proceed to completion, typically about 1 to about 5 moles of reducing agent per mole of pyrimidinyl 2'-deoxyribonucleoside is sufficient. Similarly, the amount of radical initiator should be sufficient to allow the reaction to proceed at a reasonable rate, typically about 0.005 to about 0.25 mole of radical initiator per mole of pyrimidinyl 2' -deoxyribonucleoside is sufficient, preferably about 0.01 to about 0.1 mole.

A preferred reduction step of the invention can be described as a process comprising contacting a compound of the formula

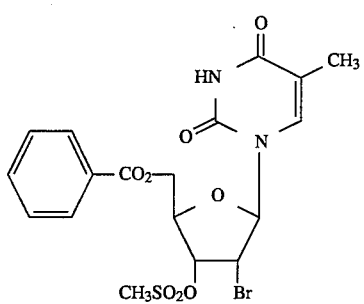

with tributyl tin hydride and a catalytic amount of azobisisobutyronitrile in ethyl acetate under conditions which result in formation of a compound of the formula

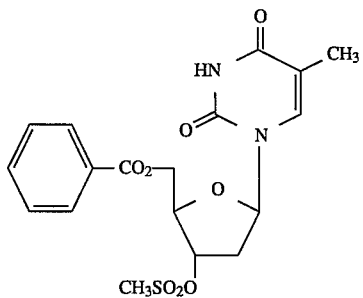

After the dehalogenated pyrimidinyl 2'-deoxyribonucleoside compound is obtained by the reduction step of the invention, it can be used as a starting material for the displacement step of the invention. The displacement step wherein the 3'-sulfonyl group has the α configuration is facile and provides superior yields as compared with prior art processes. The displacement reaction of the invention is a one-step process which avoids the need for more than one isolation and, thus, also results in improved yields. In addition, protection of the 5'-hydroxyl is optional for the displacement step. As is the case for the reduction step of the invention, the starting material for the displacement step is preferably a thymidine derivative. The displacement step requires a lithium salt as a catalyst and an azide salt to use as the displacing group. Examples of lithium salts include lithium perchlorate, lithium chloride, lithium bromide, lithium iodide, and the like. Preferred azide salts are alkali metal salts, especially $NaN_3$. The displacement step also requires the presence of a base, preferably a metal carbonate base. Preferably and conveniently, the lithium salt catalyst and the base are embodied in a single compound such as $Li_2CO_3$. Conditions for the displacement reaction are not particularly critical; for example, a temperature of about 100° C. to about 155° C. for about 2 to about 20 hours are typically adequate. The displacement reaction is performed in a solvent, preferably a polar aprotic solvent such as DMF, dimethyl sulfoxide (DMSO), N,N-dimethyl acetamide (DMAC), N-methylpyrollidinone and the like. Preferred is DMF.

The amount of lithium salt for the displacement step can be a catalytic amount. Typically, about 0.1 to about 10 moles of lithium salt (preferably about 1 to about 5 moles) are used per mole of pyrimidinyl 2'-deoxyribonucleoside. Similarly, the amount of base used is typically from about 1 to about 5 moles per mole of pyrimidinyl 2'-deoxyribonucleoside. The amount of azide salt is typically at least about 1 mole per mole of pyrimidinyl 2'-deoxyribonucleoside, preferably about 1 to about 10 moles, and more preferably about 1 to about 2 moles.

A preferred displacement step can be described as a process comprising contacting a compound of the formula

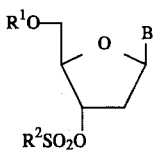

wherein $R^1$ is hydrogen or an OH-protecting group,
$R^2$ is a $C_1$–$C_{12}$ alkyl, or $C_6$–$C_{30}$ aryl, and
B is a pyrimidine base, with a base, a lithium salt, and an azide salt under conditions to result in formation of a compound of the formula

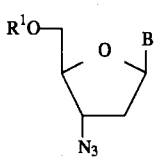

wherein $R^1$ and B are as defined hereinbefore.

An even more preferred displacement step can be described as a process comprising contacting a compound of the formula

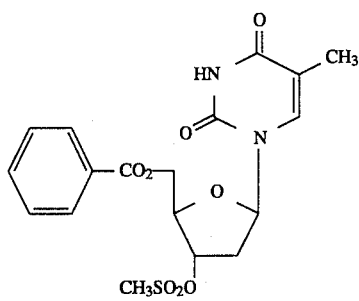

with $NaN_3$ and $Li_2CO_3$ under conditions to result in formation of the compound

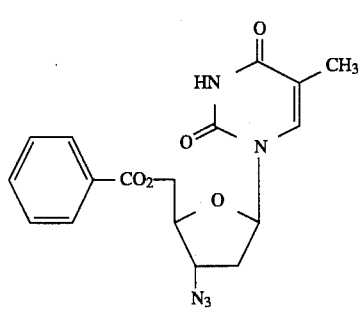

After the displacement step is performed, the 5'-protecting group can be removed by any procedure known in the art such as methanolysis to form the desired compounds, i.e., AZT or a biologically active derivative thereof. Typical methanolysis agents include sodium methoxide (NaOMe), or a mixture of methanol and a base such as trialkyl amines, NaOH and the like.

A preferred process of the invention can be described as a process comprising the steps of:

(a) contacting a 2'α,3'α,5'trihydroxy pyrimidinyl ribonucleoside with a $C_1$–$C_{12}$ alkyl or $C_6$–$C_{30}$ aryl sulfonyl chloride and a base under conditions to form a tris-(alkylsulfonyl) or tris(arylsulfonyl) compound;

(b) contacting the compound formed in step (a) with a base under conditions to form a 2,2'-anhydro compound;

(c) contacting the compound formed in step (b) with a metal carboxylate to yield a 5'-carboxylic ester compound;

(d) contacting the compound formed in step (c) with a hydrohalic acid to produce a 2'-halo- 3'-sulfonyl-5'-carboxylic diester compound;

(e) contacting the compound formed in step (d) with a tri-$C_1$–$C_{12}$ alkyl tin hydride reducing agent and a catalytic amount of a radical initiator in an ether, ester or ketone solvent to produce a 2'-deoxy-3'-sulfonyl-5'-carboxylic diester compound followed by the optional step of (f) contacting the dehalogenated compound produced in step (e) with a base, a lithium salt, and an azide salt to produce a 3'α-azido compound followed by the optional step of (g) deprotecting the compound formed in step (f) to form a compound having a 5' hydroxyl group and a 3'αazido group.

A preferred process of the invention can be depicted schematically as follows:

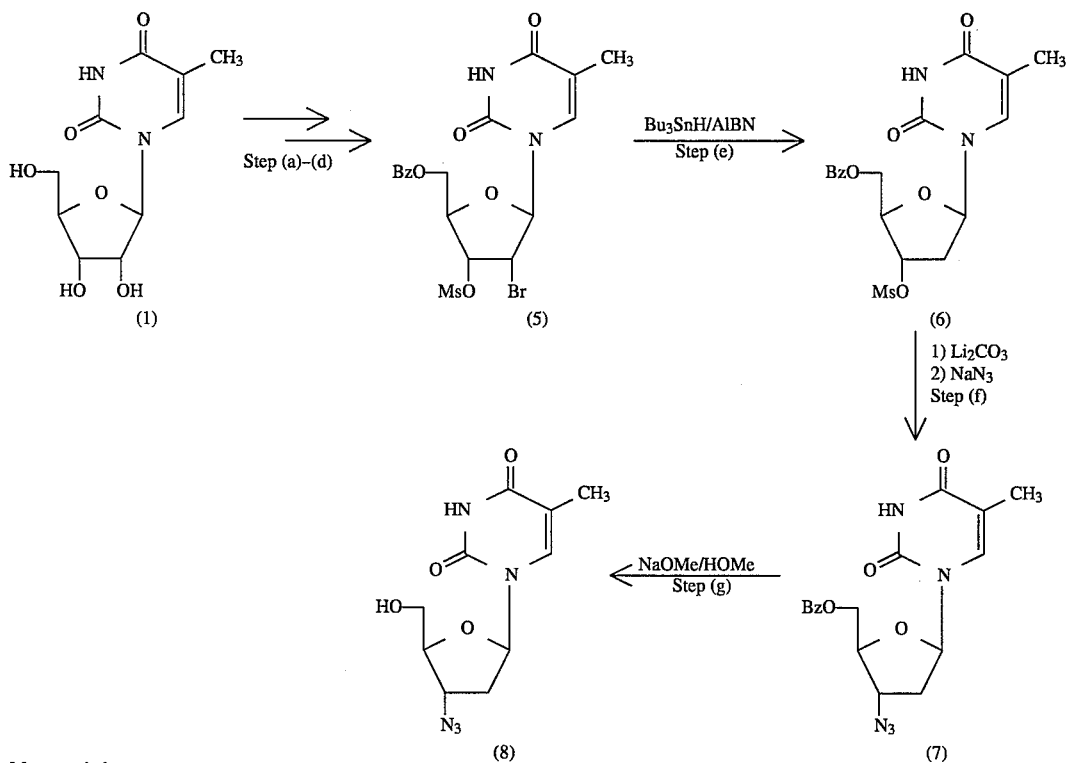

Me = methyl
Bz = benzoyl
Ms = methanesulfonyl
Bu = butyl

Some of the intermediates produced in the process of the invention are novel and, thus, the present invention also concerns these intermediates. Thus, the invention also is directed to a compound of the formula

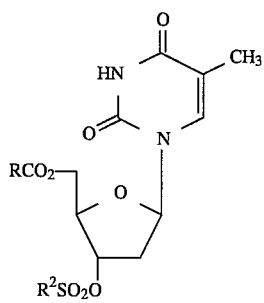

wherein

R is hydrogen, $C_1$–$C_{12}$ alkyl or $C_6$–$C_{30}$ aryl and $R^2$ is $C_1$–$C_{12}$ alkyl or $C_6$–$C_{30}$ aryl.

A preferred R group is a $C_6$–$C_{30}$ aryl, especially phenyl. A preferred compound of the invention has the formula

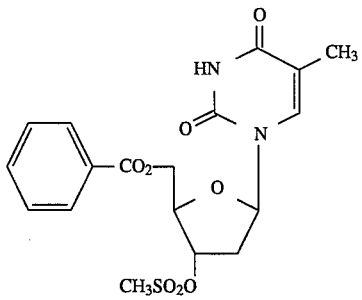

The following examples illustrate the invention but should not be interpreted as a limitation thereon.

EXAMPLE 1

2',3',5'-Tris(methanesulfonyl)-5-methyluridine (2)

To a stirred mixture of 5-methyluridine (12.8 g, 50 mmol) in pyridine (75 mL) at 0° C. was added methanesulfonyl chloride (17.4 mL, 225 mmol). The reaction mixture was stirred at 0° C. for five hours then poured into ice-water (500 mL) with stirring. Trimethanesulfonyl-5-methyluridine (2) precipitated and the mixture was stirred for 5 min. The solid product was collected by filtration and washed with water (3×200 mL) and dried. Yield, 21.6 g, 89%.

$^1$H-NMR (DMSO-$d_6$) δ 1.77 (s, 3H), 3.24 (s, 3H), 3.34 (s, 3H), 3,36 (s, 3H), 4.47–4.60 (m, 2H), 5.33 (m, 1H), 5.54 (m, 1H), 5.97 (d, J=4.5 Hz, 1H), 7.56 (s, 1H), 11.56 (s, 1H).

EXAMPLE 2

2',3',5'-Tris(methanesulfonyl)-5-methyluridine (2)

N-Methylmorpholine (29.6 mL, 266 mmol) was added to a slurry of 5-methyluridine hemihydrate (15.64 g, 58.5 mmol) in acetone (68 mL) and the resulting mixture was cooled to 5° C. A solution of methanesulfonyl chloride (20.1 mL, 255 mmol) in acetone (30 mL) was added over 45 minutes, causing the reaction temperature to rise to 45°–50° C. After stirring an additional 1.4 hours the N-methylmorpholine hydrochloride was removed by filtration and the cake was washed with acetone (2×30 mL). The combined filtrate and washes were then added to water (1L) at 10°–15° C. After stirring for 1.1 hours the white precipitate was filtered, washed with water (2×75 mL), and dried under vacuum. Yield, 27.95 g (97%).

EXAMPLE 3

5'-Benzoyl-3'-methanesulfonyl- 2,2'-anhydro-5-methyluridine (4)

To a stirred slurry of sodium benzoate (10 g, 69.3 mmol) in acetamide (50 g) at 115° C. was added trimethanesulfonyl-5-methyluridine (2) (10 g, 20.3 mmol). The reaction mixture was stirred at 115° C. for 65 min. and then poured into ice-water (2L). The mixture was stirred at 0° C. for 15 min. The white solid was filtered, washed with water (2×50 mL) and dried. Yield, 7.76 g, 90%.

$^1$H-NMR (DMSO-$d_6$) δ 1.74 (s, 3H), 3.44 (s, 3H), 4.16–4.33 (m, 2H), 4.78 (m, 1H), 5.63 (s, 1H), 5.68 (d, J=5.7 Hz, 1H), 6.45 (d, J=5.7 Hz, 1H), 7.79 (s, 1H), 7.47–7.89 (m, 5H).

EXAMPLE 4

5'-Benzoyl-3'-methanesulfonyl-2'-bromo-thymidine (5)

To a stirred mixture of 5'-benzoyl-3'-methanesulfonyl-2,2'-anhydro-5-methyluridine (4) (4.0 g, 9.5 mmol) in ethyl acetate (100 mL) and methanol (10 mL) was added acetyl bromide (5 mL, 67.7 mmol). The reaction mixture was refluxed for one hour and then cooled. The reaction mixture was transferred to a separatory funnel. Ethyl acetate (150 mL) was added. The solution was washed with saturated sodium bicarbonate (100 mL) followed by brine (100 mL). The organic layer was separated and dried over MgSO$_4$. Removal of solvent gave the solid product 5. Yield, ⁻4.86 g, 100%.

$^1$H-NMR (DMSO-$d_6$) δ 1.63 (s, 3H), 3.37 (s, 3H), 4.50–4.55 (m, 2H), 4.60–4.64 (m, 2H), 5.09 (t, J=6.0 Hz, 1H), 5.47 (m, 1H), 6.14 (d, J=7.2 Hz, 1H), 7.49 (s, 1H), 7.50–8.04 (m, 5H), 11.56 (s, 1H).

EXAMPLES 5–11

5'-Benzoyl-3'-methanesulfonylthymidine (6) (reduction step)

General Procedure: To a 50 ml round-bottom flask equipped with condenser, nitrogen inlet, and thermometer was added 5'-benzoyl-3'-methanesulfonyl-2'-bromo-thymidine (5) (3.0 g, 5.96 mmol) and 30 ml of the specified solvent (see the table below). Bu$_3$SnH (3.0 ml, 11.15 mmol; 1.9 equiv) was then added. The reaction mixture was heated to reflux or to the temperature specified in the table, to give a clear, homogeneous solution. The reaction mixture was then cooled slightly and 300 mg AIBN was added. The mixture was heated to reflux or the temperature specified in table for 45 minutes at which time the reaction was complete by HPLC (or for a period of time as specified in the table).

The mixture was then cooled to 25° C. and concentrated to give a residue. The residue was purified by silica gel column chromatography (Kiesgel 60, 230–400 mesh silica gel, 2.5× 23 cm column, 3/1 EtOAc/hexane as eluent) or by methylene chloride trituration to afford 5'-benzoyl-3'-methanesulfonylthymidine (6). These results were summarized in the table.

TABLE

Reductions of 5'-benzoyl-3'-methanesulfonyl-2'-bromothymidine (5) to 5'-benzoyl-3'-methanesulfonylthymidine (6):

| EXAMPLE | Solvent | Temp (°C.) | Time | Impurity (%)[a] | Yield (%) |
|---|---|---|---|---|---|
| 5 | THF | 67° C. | 45 min | <0.05 | 94[b] |
|   |     | 67° C. | 2.0 h | <0.05 | 76[c] |
| 6 | EtOAc | 78° C. | 45 min | <0.05 | 87[c] |
|   |       | 78° C. | 2.0 h | <0.05 | d |
| 7 | Acetone | 56° C. | 2.0 h | 0.20 | 84[b] |
| 8 (comparative) | EtOH | 76° C. | 45 min | 6.70 | 79[b] |
|   |      |        | 2.5 h | 7.20 | 48[c] |
| 9 (comparative) | Toluene | 80–90° C. | 45 min | 1.20 | 91[b] |
|   |         |         | 2.0 h | 12.6 | d |
|   |         |         | 6.0 h | 21.6 | 100[c,e] |
| 10 (comparative) | DMAC | 80–90° C. | 45 min | 6.90 | 56[b] |
| 11 (comparative) | DMF | 80–90° C. | 45 min | 17.3 | 83[b] |
|   |     | 125–130° C. | 2.5 h | 24.2 | d |

[a]Impurity (%) represents HPLC area % of the impurity in the reaction mixture. The impurity was identified as 5'-benzoyl-2,3'-anhydrothymidine.
[b]Weight yield (%) isolated by silica gel column chromatographic separation.

[c]Weight yield (%) isolated by methylene chloride trituration. This isolation method did not purge the impurity from the desired product (6). This preferred isolation method was only practical for those cases where the reaction (reduction step) was clean (little or no impurity formation).
[d]Product (6) not isolated.
[e]High yield also due to tributyltin bromide contamination.

The following are additional information for the results given in the table:

Example #5

Use of THF (tetrahydrofuran) resulted in <0.05% of the impurity by HPLC even after 2 h at reflux (67° C.). The product (6) was isolated by silica gel column chromatography in 94% yield. Isolation by methylene chloride trituration gave a 76% yield.

$^1$H-NMR (DMSO-$d_6$) δ 1.57 (s, 3H), 2.55 (m, 2H), 3.32 (s, 3H), 4.45 (s, 1H), 4.48–4.60 (m, 2H), 5.47 (m, 1H), 6.22 (t, J=6.9 Hz, 1H), 7.41 (s, 1H), 7.52–8.02 (m, 5H), 11.40 (s, 1H).

Example #6

Use of ethyl acetate resulted in <0.05% of the impurity by HPLC even after 2.5 h at reflux (78° C.). The product (6) was isolated by methylene chloride trituration in 87% yield.

Example #7

Use of acetone resulted in 0.20% HPLC area of the impurity after 2 hours at reflux (56° C.). The product (6) was isolated by silica gel column chromatography in 84% yield.

Example #8 (comparative)

Use of ethanol resulted in 6.7% HPLC area of the impurity in 45 minutes at reflux (76° C.). At 2.5 h, the level of impurity increased to 7.2%. The product (6) was isolated by silica gel column chromatography in 79%. Isolation by methylene chloride trituration resulted in a 48% yield of product (6) containing 7.0% (HPLC area) of the impurity.

Example #9 (comparative)

Use of toluene as solvent in the reduction resulted in 1.2% HPLC area of the impurity at 80°–90° C. in 45 minutes. The product was isolated by column chromatography giving a 91% yield. In a separated experiment using toluene, the reaction mixture contained 12.6% HPLC area of the impurity at 80°–90° C. in 2 hours and 21.6% area after 4 additional hours. The product was isolated by methylene chloride trituration in essentially a quantitative yield but the product contained 26.3% (HPLC area) of the impurity. The product was also contaminated with tributyltin bromide, as indicated by $^1$H-NMR.

Example #10 (comparative)

Use of dimethylacetamide (DMAC) resulted in 6.9% HPLC area of the impurity in 45 minutes at 80°–90° C. The product was isolated by silica gel column chromatography in 56% yield.

Example #11 (comparative)

Use of DMF (dimethylformamide) resulted in 17.3% HPLC area of the impurity at 80°–90° C. in 45 minutes. The product was isolated by silica gel column chromatography in 83% yield. In a separated experiment using DMF, a 24.2% HPLC area of the impurity was detected at 2.5 h at 125°–130° C.

EXAMPLE 12

5'-Benzoyl-3'α-azido-3'-deoxythymidine (7) (displacement step)

To the stirred solution of 5'-benzoyl-3'-methanesulfonylthymidine (6) (0.5 g, 1.18 mmol) in DMF (3 ml) was added lithium carbonate (0.2 g, 2.7 mmol). The reaction mixture was placed in a preheated oil bath at 125° C. and stirred for 100 minutes. Sodium azide (0.2 g, 3.1 mmol) was then added and the reaction was stirred at 125° C. for five hours. The reaction mixture was then cooled to room temperature and poured into ice-water (5 ml). The pH was adjusted to ca. 6 by adding acetic acid. The resulting precipitate was collected by filtration and dried to give 5'-benzoyl-3'α-azido-3'-deoxythymidine (7). Yield, 0.37 g (82%).

$^1$H-NMR (CDCl$_3$): δ 1.64 (s, 3H), 2.32–2.55 (m, 2H), 4.18 (m, 1H), 4.32 (m, 1H), 4.50–4.67 (m, 2H), 6.15 (t, J=6.4 Hz, 1H), 7.16 (s, 1H), 7.41–8.01 (m, 5H), 9.54 (s, 1H).

EXAMPLE 13

3'α-Azido-3'-deoxythymidine (8)

To the stirred solution of 5'-benzoyl-3'α-azido-3'-deoxythymidine (7) (0.20 g, 0.54 mmol) in methanol (3 ml) was added 25% sodium methoxide solution in methanol (0.4 ml, 1.75 mmol). The reaction was stirred at room temperature for one hour and the mixture was then neutralized by strong acidic resin (Dowex 50-200X8, prewashed with methanol) to a pH of ca. 6. The resin was filtered off and washed with methanol (2×10 ml). The solvent was removed to give AZT which was dried under vacuum. Yield, 0.10 g (71%).

$^1$H-NMR (D$_2$O) δ 1.70 (s, 3H), 2.32 (t, J=6.5 Hz, 2H), 3.58–3.71 (m, 2H), 3.83 (q, J=4.7 Hz, 1H), 4.18 (q, J=6.4 Hz, 1H), 6.02 (t, J=6.5 Hz, 1H), 7.46 (s, 1H).

We claim:

1. A process for preparing a dehalogenated pyrimidinyl 2'-deoxyribonucleoside comprising reacting a 2'-deoxy-2'-halo- 5'-protected pyrimidinyl ribonucleoside having a 3'-sulfonyl group with a tri($C_1$–$C_{12}$alkyl) tin hydride reducing agent and a catalytic amount of a radical initiator in an ether, ester or ketone solvent under suitable conditions to yield said dehalogenated pyrimidinyl 2'-deoxyribonucleoside.

2. The process of claim 1 wherein the pyrimidinyl group is thymidine.

3. The process of claim 1 wherein the solvent is an ether containing two to ten carbon atoms, an ester containing two to ten carbon atoms, or a ketone containing three to ten carbon atoms.

4. The process of claim 1 wherein the solvent is $C_1$–$C_4$ alkyl ether, a $C_4$–$C_6$ cylic ether, a $C_2$–$C_6$ alkyl ester, or a $C_3$–$C_6$ dialkyl ketone.

5. The process of claim 1 wherein the solvent is selected from the group consisting of methyl acetate, ethyl acetate, butyl acetate, propyl acetate, isopropyl acetate, t-butyl acetate, s-butyl acetate, ethyl formate, tetrahydrofuran, dibutyl ether, diethyl ether, methyl t-butyl ether, acetone, butanone, pentanone, methyl isobutyl ketone, amyl acetate, cyclohexanone, dioxane, 1,2-dimethoxyethane, 1,2-diethoxyethane and diethoxymethane.

6. The process of claim 1 wherein the solvent is selected from the group consisting of ethyl acetate, butyl acetate, acetone, and tetrahydrofuran.

7. The process of claim 1 wherein the radical initiator is selected from the group consisting of azobisisobutyronitrile, di-t-butyl peroxide, benzoyl peroxide, t-butyl peracetate or diacetyl peroxide.

8. The process of claim 1 wherein the tri($C_1$–$C_{12}$alkyl) tin hydride is tributyl tin hydride and the radical initiator is azobisisobutyronitrile.

9. The process of claim 1 wherein the 5'-protecting group is a carboxylic ester.

10. The process of claim 1 wherein the 5'-protecting group is benzoyl.

11. The process of claim 1 the 3'-sulfonyl group is $C_1$–$C_{12}$alkylsulfonyl or $C_6$–$C_{30}$ arylsulfonyl.

12. The process of claim 1 wherein the 2'-halo group is Br.

13. The process of claim 1 wherein in reaction is carried out at a temperature of about 50° C. to about 125° C. for about 0.25 to 5 hours.

14. A process for preparing a nucleoside of the following formula I:

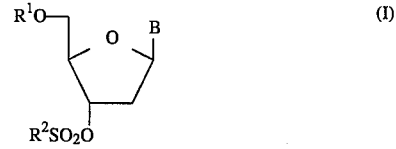

wherein $R^1$ is hydrogen or a hydroxyl protecting group $R^2$ is $C_1$–$C_{12}$alkyl or $C_6$–$C_{30}$aryl B is a pyrimidine base;

comprising reacting a compound of the formula II:

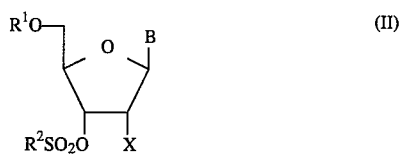

with a tri($C_1$–$C_{12}$alkyl) tin hydride reducing agent and a catalytic amount of a radical initiator in a ether, ester, or ketone solvent under suitable conditions to yield a nucleoside of formula I, and wherein X is Cl, Br, or I.

15. A process for the preparation of 3'-mesyl-5'-benzoylthymidine having the following formula (III)

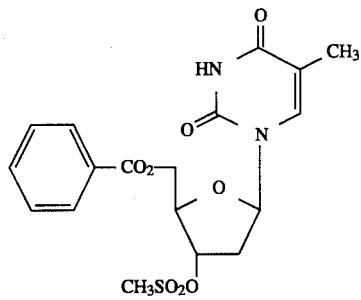

(III)

comprising contacting a nucleoside of formula IV:

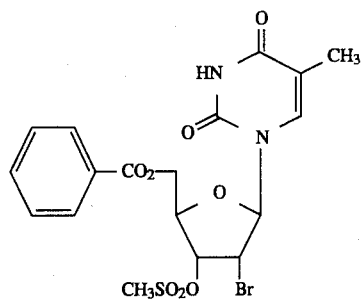

(IV)

with tributyl tin hydride and a catalytic amount of azobisisobutyronitrile in ethyl acetate under suitable conditions which result in formation 3'-mesyl-5'-benzoyl thymidine.

16. A process for preparing a 5'-protected pyrimidinyl 2',3'-dideoxy-3'-azido-ribonucleoside comprising the steps of:
(a) reacting a 2'-halo-5'-protected pyrimidinyl 2'-deoxyribonucleoside having a 3'-sulfonyl group with a tri($C_1$–$C_{12}$ alkyl) tin hydride reducing agent and a catalytic amount of a radical initiator in an ether, ester, or ketone solvent under suitable conditions to yield a dehalogenated pyrimidinyl 2'-deoxyribonucleoside;

followed by
(b) reacting said dehalogenated pyrimidinyl 2'-deoxynucleoside formed in step (a) with a base, a lithium salt, and an azide salt under suitable conditions to yield the 5'-protected pyrimidinyl 2',3'-dideoxy-3'-azidoribonucleoside.

17. The process of claim 16 further comprising step
(c) deprotecting the 5'-protected pyrimidinyl 2',3'-dideoxyribonucleoside formed in step (b) to yield the unprotected pyrimidinyl 2',3' -dideoxy-3'-azido-ribonucleoside.

18. A process for preparing 2'-deoxy-3'sulfonyl-5'-acyl pyrimidinyl ribonucleoside comprising
(a) reacting a 2',3',5'-trihydroxy pyrimidinyl ribonucleoside with a $C_1$–$C_{12}$alkyl or $C_6$–$C_{30}$ arylsulfonyl chloride and a base under suitable conditions to yield a 2',3',5'-tris(alkylsulfonyl) or a 2',3',5'-tris(arylsulfonyl) ribonucleoside;
(b) reacting the nucleoside formed in step (a) with a base under suitable conditions to form O2,2'-anhydro-3'-sulfonyl-pyrimidinyl ribonucleoside;
(c) reacting the nucleoside formed in step (b) with a metal carboxylate to yield a 5' -5'-acyl-O2,2'-anhydro-3'-sulfonyl-pyrimidinyl ribonucleoside; and
(d) reacting the nucleoside formed in step (c) with a hydrohalic acid to produce a 2'-deoxy- 2'-halo-3'-sulfonyl-5'-acyl-pyrimidinyl ribonucleoside;
(e) reacting the nucleoside formed in step (d) with tri($C_1$–$C_{12}$alkyl) tin hydride reducing agent and a catalytic amount of a radical initiator in an ether, ester or ketone solvent to produce the 2'-deoxy-3'-sulfonyl-5'-acyl-pyrimidinyl ribonucleoside.

19. The process of claim 18 further comprising the step of
f) reacting the halogenated nucleoside of step (e) with a base, a lithium salt, and an azide salt to yield 2'3,'-dideoxy-3'-azido-5'-acylpyrimidinyl ribonucleoside.

20. The process of claim 19 further comprising the step of
(g) deprotecting the nucleoside formed in step (f) to produce 2',3'-dideoxy-3'-azido-pyrimidinyl ribonucleoside.

* * * * *